United States Patent
Wang (10) Patent No.: US 11,207,024 B2
(45) Date of Patent: Dec. 28, 2021

(54) VASCULAR IMAGING APPARATUS AND VASCULAR IMAGING METHOD

(71) Applicant: BOE TECHNOLOGY GROUP CO., LTD., Beijing (CN)

(72) Inventor: Guohe Wang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 538 days.

(21) Appl. No.: 16/314,090

(22) PCT Filed: Jan. 30, 2018

(86) PCT No.: PCT/CN2018/074515
§ 371 (c)(1),
(2) Date: Dec. 28, 2018

(87) PCT Pub. No.: WO2019/010958
PCT Pub. Date: Jan. 17, 2019

(65) Prior Publication Data
US 2021/0228151 A1    Jul. 29, 2021

(30) Foreign Application Priority Data
Jul. 12, 2017  (CN) .......................... 201710566270.2

(51) Int. Cl.
*A61B 5/00*      (2006.01)
*G06T 7/00*      (2017.01)
*A61B 90/00*     (2016.01)

(52) U.S. Cl.
CPC ............ *A61B 5/489* (2013.01); *A61B 5/0082* (2013.01); *G06T 7/0012* (2013.01);
(Continued)

(58) Field of Classification Search
CPC ..... A61B 5/489; A61B 5/0064; A61B 5/0082; A61B 2090/366; G06T 7/0012–0016
See application file for complete search history.

(56) References Cited

U.S. PATENT DOCUMENTS 3,899,149 A * 8/1975 Schneider ............ A61G 7/0503
                                                              248/75
3,998,210 A * 12/1976 Nosari ...................... A61B 5/01
                                                              600/549
(Continued)

FOREIGN PATENT DOCUMENTS

CN       202821303 U     3/2013
CN       203314943 U    12/2013
(Continued)

OTHER PUBLICATIONS

Nishidate et al., "Topographic Imaging of Veins Using Reflectance Images at Isosbestic Wavelengths", SICE Annual Conference in Sapporo, August 44,2004, Hokkaido Institute of Technology, Japan, pp. 2145-2148 (Year: 2004).*

(Continued)

*Primary Examiner* — James M Kish (57) ABSTRACT

A vascular imaging apparatus and a vascular imaging method are disclosed. The vascular imaging apparatus includes: a light source device, an image acquisition device, a projection device and an image processor. The light source device is configured to emit visible light and infrared light to a body portion to be tested in a time-sharing manner; the image acquisition device is configured to receive the visible light and the infrared light reflected by the body portion to be tested to acquire a visible image and an infrared image respectively; the image processor is configured to perform image processing on the infrared image and the visible image, to acquire a vascular enhancement image of the body portion to be tested; the projection device is configured to project the vascular enhancement image onto the body portion to be tested.

17 Claims, 4 Drawing Sheets

(52) U.S. Cl.
CPC ......... *A61B 2090/366* (2016.02); *G06T 2207/10004* (2013.01); *G06T 2207/10048* (2013.01); *G06T 2207/30101* (2013.01)

(56) References Cited

U.S. PATENT DOCUMENTS

| | | | | | |
|---|---|---|---|---|---|
| 4,619,249 | A * | 10/1986 | Landry | ............... | A61B 5/0059 362/199 |
| 4,817,622 | A * | 4/1989 | Pennypacker | ......... | A61B 5/489 600/473 |
| RE33,234 | E * | 6/1990 | Landry | ............... | A61B 5/0059 362/199 |
| 5,339,817 | A * | 8/1994 | Nilsson | ............... | A61B 5/0261 600/473 |
| 5,361,769 | A * | 11/1994 | Nilsson | ............... | A61B 5/0261 356/28 |
| 5,519,208 | A * | 5/1996 | Esparza | ............... | A61B 5/0059 250/226 |
| 5,603,328 | A * | 2/1997 | Zucker | ............... | A61B 5/015 250/330 |
| 5,608,210 | A * | 3/1997 | Esparza | ............... | A61B 5/0059 250/226 |
| 5,678,555 | A * | 10/1997 | O'Connell | ............... | A61B 5/01 600/473 |
| 5,772,593 | A * | 6/1998 | Hakamata | ............. | A61B 90/36 348/77 |
| 5,787,185 | A * | 7/1998 | Clayden | ............... | A61B 5/1171 382/115 |
| 5,876,346 | A * | 3/1999 | Corso | ............... | A61B 5/742 600/485 |
| 5,969,754 | A * | 10/1999 | Zeman | ............... | G09B 21/008 348/136 |
| 6,032,070 | A * | 2/2000 | Flock | ............... | A61B 5/0059 600/310 |
| 6,056,692 | A * | 5/2000 | Schwartz | ............... | A61B 8/08 600/443 |
| 6,178,340 | B1 * | 1/2001 | Svetliza | ............... | A61B 5/0059 600/310 |
| 6,230,046 | B1 * | 5/2001 | Crane | ............... | A61B 5/445 600/476 |
| 6,263,227 | B1 * | 7/2001 | Boggett | ............... | A61B 5/0261 356/39 |
| 6,301,375 | B1 * | 10/2001 | Choi | ............... | G06K 9/00 382/115 |
| 6,424,858 | B1 * | 7/2002 | Williams | ............. | A61B 5/0059 250/330 |
| 6,443,928 | B1 * | 9/2002 | Francis | ............... | A61M 5/3287 604/116 |
| 6,463,309 | B1 * | 10/2002 | Ilia | ...................... | A61B 5/0059 382/128 |
| 6,464,646 | B1 * | 10/2002 | Shalom | ............... | A61B 5/489 600/549 |
| 6,522,911 | B1 * | 2/2003 | Toida | ............... | A61B 5/0059 356/319 |
| 6,542,246 | B1 * | 4/2003 | Toida | ............... | A61B 5/0059 356/484 |
| 6,556,854 | B1 * | 4/2003 | Sato | ............... | A61B 5/0059 356/27 |
| 6,556,858 | B1 * | 4/2003 | Zeman | ............... | H04N 5/2354 600/473 |
| 6,599,247 | B1 * | 7/2003 | Stetten | ............... | A61B 8/00 128/916 |
| 6,631,286 | B2 * | 10/2003 | Pfeiffer | ............... | A61B 5/0059 348/E5.029 |
| 6,690,964 | B2 * | 2/2004 | Bieger | ............... | A61B 90/36 600/407 |
| 6,923,762 | B1 * | 8/2005 | Creaghan, Jr. | ....... | A61B 5/0059 362/231 |
| 7,158,660 | B2 * | 1/2007 | Gee, Jr. | ............... | A61B 5/0059 382/128 |
| 7,239,909 | B2 * | 7/2007 | Zeman | ............... | A61B 5/0059 600/473 |
| 7,841,751 | B2 * | 11/2010 | Mulani | ............... | A61B 5/0059 362/362 |
| 7,874,698 | B2 * | 1/2011 | Mullani | ............... | A61B 5/0059 362/230 |
| 7,904,138 | B2 * | 3/2011 | Goldman | ............... | A61B 5/743 600/473 |
| 7,983,738 | B2 * | 7/2011 | Goldman | ............... | A61B 5/0059 600/476 |
| 8,032,205 | B2 * | 10/2011 | Mullani | ............. | G01N 21/8803 600/476 |
| 8,255,040 | B2 * | 8/2012 | Goldman | ............... | A61B 5/0059 600/473 |
| 8,364,246 | B2 * | 1/2013 | Thierman | ............... | A61B 5/0062 600/476 |
| 8,380,291 | B2 * | 2/2013 | Wood | ..................... | A61B 5/489 600/476 |
| 8,463,364 | B2 * | 6/2013 | Wood | ..................... | A61B 5/0064 600/473 |
| 8,489,178 | B2 * | 7/2013 | Wood | ..................... | A61B 5/0064 600/473 |
| 8,494,616 | B2 * | 7/2013 | Zeman | ............... | A61B 5/0077 600/473 |
| 8,594,770 | B2 * | 11/2013 | Wood | ..................... | A61B 5/0075 600/476 |
| 8,665,507 | B2 * | 3/2014 | Luciano | ............... | A61B 5/0062 359/224.1 |
| 8,730,321 | B2 * | 5/2014 | Luciano | ............... | H04N 9/3194 348/135 |
| 9,028,421 | B2 * | 5/2015 | Fujii | ................... | A61B 3/1233 600/504 |
| 9,061,109 | B2 * | 6/2015 | Wood | ..................... | A61B 5/7225 |
| 9,072,426 | B2 * | 7/2015 | Zott | ..................... | A61B 5/0033 |
| 9,492,117 | B2 * | 11/2016 | Goldman | ............. | A61B 5/0064 |
| 9,788,787 | B2 * | 10/2017 | Goldman | ............. | A61B 5/0075 |
| 9,788,788 | B2 * | 10/2017 | Goldman | ............. | A61B 5/0068 |
| 9,789,267 | B2 * | 10/2017 | Wood | ..................... | A61B 5/0062 |
| 9,949,688 | B2 * | 4/2018 | Goldman | ............... | A61M 5/46 |
| 10,238,294 | B2 * | 3/2019 | Wood | ..................... | A61B 5/0079 |
| 2002/0016533 | A1 * | 2/2002 | Marchitto | ............ | A61B 5/0066 600/310 |
| 2003/0018271 | A1 * | 1/2003 | Kimble | ............... | A61B 5/0059 600/473 |
| 2003/0047683 | A1 * | 3/2003 | Kaushal | ............... | A61B 5/01 250/330 |
| 2003/0120154 | A1 * | 6/2003 | Sauer | ..................... | A61B 8/461 600/459 |
| 2003/0199765 | A1 * | 10/2003 | Stetten | ............... | A61B 8/5238 600/439 |
| 2004/0022421 | A1 * | 2/2004 | Endoh | ..................... | G06F 21/32 382/115 |
| 2004/0171923 | A1 * | 9/2004 | Kalafut | ............... | A61G 13/12 600/407 |
| 2005/0143662 | A1 * | 6/2005 | Marchitto | ............ | A61B 5/0071 600/473 |
| 2005/0154303 | A1 * | 7/2005 | Walker | ............... | G01S 7/52061 600/443 |
| 2005/0157939 | A1 * | 7/2005 | Arsenault | ............... | G06T 5/002 382/260 |
| 2005/0281445 | A1 * | 12/2005 | Marcotte | ............... | G06T 5/004 382/128 |
| 2006/0020212 | A1 * | 1/2006 | Xu | ..................... | A61B 5/0059 600/473 |
| 2006/0122515 | A1 * | 6/2006 | Zeman | ............... | H04N 5/33 600/473 |
| 2006/0129037 | A1 * | 6/2006 | Kaufman | ............. | A61B 5/1455 600/322 |
| 2006/0129038 | A1 * | 6/2006 | Zelenchuk | ......... | A61B 5/14535 600/322 |
| 2006/0173351 | A1 * | 8/2006 | Marcotte | ............ | A61B 17/3403 600/473 |
| 2006/0173360 | A1 * | 8/2006 | Kalafut | ............... | A61B 5/0059 600/478 |
| 2006/0176242 | A1 * | 8/2006 | Jaramaz | ............... | A61B 34/20 345/7 |
| 2008/0147147 | A1 * | 6/2008 | Griffiths | ............... | A61B 5/489 607/88 |

(56) References Cited

U.S. PATENT DOCUMENTS

| | | | | |
|---|---|---|---|---|
| 2008/0194930 | A1* | 8/2008 | Harris | A61B 90/36 600/310 |
| 2008/0221519 | A1* | 9/2008 | Schwach | A61B 8/4209 604/116 |
| 2009/0018414 | A1* | 1/2009 | Toofan | A61B 5/0059 600/310 |
| 2009/0245601 | A1* | 10/2009 | Cohen | A61B 5/489 382/128 |
| 2010/0079825 | A1* | 4/2010 | Yamazaki | G02B 27/46 358/474 |
| 2010/0225927 | A1* | 9/2010 | Dillon | A61B 5/0084 356/511 |
| 2011/0301500 | A1* | 12/2011 | Maguire | A61B 34/30 600/583 |
| 2012/0071765 | A1* | 3/2012 | Chinnock | A61B 5/0075 600/476 |
| 2012/0190981 | A1* | 7/2012 | Harris | A61B 5/150389 600/439 |
| 2013/0006112 | A1* | 1/2013 | Vardy | A61B 5/489 600/443 |
| 2013/0006178 | A1* | 1/2013 | Pinho | A61B 5/0059 604/116 |
| 2013/0018254 | A1* | 1/2013 | Drucker | A61B 5/0077 600/424 |
| 2014/0100455 | A1* | 4/2014 | Goldman | A61B 5/150748 600/427 |
| 2014/0187966 | A1* | 7/2014 | Thierman | A61B 5/0059 600/473 |
| 2016/0128627 | A1* | 5/2016 | Demos | A61B 5/0059 600/473 |
| 2016/0262626 | A1* | 9/2016 | Pelosi | A61B 5/0059 |
| 2016/0317080 | A1* | 11/2016 | Smith | A61B 5/489 |
| 2018/0005085 | A1* | 1/2018 | Kakileti | G06K 9/6267 |
| 2018/0295296 | A1* | 10/2018 | Huang | A61B 5/489 |

FOREIGN PATENT DOCUMENTS

| | | | | |
|---|---|---|---|---|
| CN | 103584836 | A | 2/2014 | |
| CN | 104665767 | A | 6/2015 | |
| CN | 105116114 | A | 12/2015 | |
| CN | 105848566 | A | 8/2016 | |
| CN | 205507277 | U | 8/2016 | |
| CN | 106037674 | A | 10/2016 | |
| CN | 106878040 | A | 5/2017 | |
| CN | 107049254 | A | 8/2017 | |
| WO | WO 2014094173 | A1 * | 6/2014 | A61B 6/00 |
| WO | 2016/153741 | A1 | 9/2016 | |

OTHER PUBLICATIONS

International Search Report and Written Opinion dated May 7, 2018; PCT/CN2018/074515.

Extended European Search Report dated Mar. 15, 2021; Appln. No. 18815495.9.

The First Chinese Office Action dated Jan. 3, 2020; Appln. No. 201710566270.2.

* cited by examiner

VASCULAR IMAGING APPARATUS AND VASCULAR IMAGING METHOD

CROSS-REFERENCE TO RELATED APPLICATION

The present application claims priority of the Chinese Patent Application No. 201710566270.2, filed on Jul. 12, 2017, the disclosure of which is incorporated herein by reference in its entirety as part of the present application.

TECHNICAL FIELD

The embodiments of the present disclosure relate to a vascular imaging apparatus and a vascular imaging method.

BACKGROUND

Venipuncture is one of conventional therapy measures in a clinical medical field, and the venipuncture can be used for clinical intravenous administration, blood transfusion, infusion, blood drawing, and the like. During a venipuncture process, positioning of veins mainly relies on experience of a medical staff, who makes a blood vessel to bulge by tying an arm, and judges through touch with fingers and direct visual observation. Because venous blood vessels of infants, elderly patients, dark-skinned patients or obese patients are not clear, it is difficult for the medical staff to perform venipuncture successfully on the first try, and the medical staff often requires to perform venipuncture operations many times.

SUMMARY

An embodiment of the present disclosure discloses a vascular imaging apparatus, which comprises: a light source device, an image acquisition device, a projection device and an image processor. The light source device is configured to emit visible light and infrared light to a body portion to be tested in a time-sharing manner; the image acquisition device is configured to receive the visible light reflected by the body portion to be tested to acquire a visible image, receive the infrared light reflected by the body portion to be tested to acquire an infrared image, and transmit the infrared image and the visible image to the image processor; the image processor is configured to receive the infrared image and the visible image, and perform image processing on the infrared image and the visible image, to acquire a vascular enhancement image of the body portion to be tested, and the image processor is further configured to transmit the vascular enhancement image to the projection device; and the projection device is configured to receive the vascular enhancement image and project the vascular enhancement image onto the body portion to be tested.

For example, in the vascular imaging apparatus provided by an embodiment of the present disclosure, the image processor is configured to perform vascular recognition processing on the visible image and the infrared image, to respectively acquire a vascular region and a non-vascular region in the infrared image, a vascular region and a non-vascular region in the visible image, calculate a ratio of an average light intensity value of the non-vascular region in the infrared image to an average light intensity value of the non-vascular region in the visible image, and calculate a product of a light intensity value of the visible image and the ratio, and perform difference processing on a light intensity value of the infrared image and the product, to acquire the vascular enhancement image.

For example, in the vascular imaging apparatus provided by an embodiment of the present disclosure, a method of the vascular recognition processing is a multi-scale Hessian matrix method.

For example, in the vascular imaging apparatus provided by an embodiment of the present disclosure, the light source device comprises a visible light source, an infrared light source and a light source conversion element, the visible light source is configured to emit the visible light, the infrared light source is configured to emit the infrared light, and the light source conversion element is configured to allow a position at which the visible light is incident on the body portion to be tested and a position at which the infrared light is incident on the body portion to be tested to be same.

For example, in the vascular imaging apparatus provided by an embodiment of the present disclosure, the light source conversion element comprises a light source driver, a first light source connecting rod and a second light source connecting rod, one end of the first light source connecting rod is connected with the infrared light source, and the other end is connected with the light source driver, one end of the second light source connecting rod is connected with the visible light source, and the other end is connected with the light source driver, and the light source driver is configured to move the visible light source or the infrared light source to a light source target position in a time-sharing manner.

For example, in the vascular imaging apparatus provided by an embodiment of the present disclosure, the light source conversion element comprises a dichroic mirror, the infrared light source and the visible light source are symmetrically provided with respect to the dichroic mirror, a position at which the infrared light emitted via the dichroic mirror is incident on the body portion to be tested is identical to a position at which the visible light emitted via the dichroic mirror is incident on the body portion to be tested.

For example, the vascular imaging apparatus provided by an embodiment of the present disclosure further comprises a reflecting-mirror device, the projection device and the image acquisition device are symmetrical with respect to the reflecting-mirror device, and the reflecting-mirror device is configured to reflect light projected by the projection device to the body portion to be tested.

For example, in the vascular imaging apparatus provided by an embodiment of the present disclosure, the reflecting-mirror device comprises a reflecting-mirror, a reflecting-mirror driver and a reflecting-mirror connecting rod, one end of the reflecting-mirror connecting rod is connected with the reflecting-mirror, and the other end is connected with the reflecting-mirror driver, the reflecting-mirror driver is configured to move the reflecting-mirror to a non-reflective position or a reflective position, the reflecting-mirror is configured to reflect the light projected by the projection device to the body portion to be tested in a case where the reflecting-mirror is located in the reflective position, and the image acquisition device is configured to receive the visible light or the infrared light reflected by the body portion to be tested in a case where the reflecting-mirror is located in the non-reflective position.

For example, in the vascular imaging apparatus provided by an embodiment of the present disclosure, the light projected by the projection device is red light or green light.

For example, the vascular imaging apparatus provided by an embodiment of the present disclosure further comprises a lens group, the lens group is located on a light exiting side of the light source device, and is configured to converge the visible light and the infrared light.

For example, the vascular imaging apparatus provided by an embodiment of the present disclosure further comprises an optical filter group, the optical filter group comprises an infrared light filter, a visible light filter and an optical filter driver, the optical filter driver is configured to move the visible light filter to an image input end of the image acquisition device in a case where the light source device emits the visible light, and the optical filter driver is configured to move the infrared light filter to the image input end of the image acquisition device in a case where the light source device emits the infrared light.

For example, in the vascular imaging apparatus provided by an embodiment of the present disclosure, the visible light has a wavelength ranging from 0.63 μm to 0.76 μm, and the infrared light has a wavelength ranging from 0.85 μm to 0.95 μm.

For example, the vascular imaging apparatus provided by an embodiment of the present disclosure further comprises a controller, the controller is configured to control the light source device to emit the visible light and the infrared light in a time-sharing manner.

An embodiment of the present disclosure further discloses a vascular imaging method, which comprises: time-divisionally using infrared light and visible light to illuminate a body portion to be tested; acquiring an infrared image and a visible image of the body portion to be tested; performing image processing on the infrared image and the visible image, to acquire a vascular enhancement image of the body portion to be tested; and projecting the vascular enhancement image to the body portion to be tested.

For example, in the vascular imaging method provided by an embodiment of the present disclosure, performing image processing on the infrared image and the visible image comprises: performing vascular recognition processing on the visible image and the infrared image; calculating a ratio of an average light intensity value of a non-vascular region in the infrared image to an average light intensity value of a non-vascular region in the visible image; and calculating a product of a light intensity value of the visible image and the ratio, and performing difference processing on a light intensity value of the infrared image and the product.

For example, in the vascular imaging method provided by an embodiment of the present disclosure, a method of the vascular recognition processing is a multi-scale Hessian matrix method.

For example, in the vascular imaging method provided by an embodiment of the present disclosure, acquiring an infrared image and a visible image comprises: moving a reflecting-mirror to a non-reflective position; moving an infrared light source to a light source target position, emitting the infrared light to the body portion to be tested by the infrared light source, and receiving the infrared light reflected by the body portion to be tested to acquire the infrared image; and moving a visible light source to the light source target position, emitting the visible light to the body portion to be tested by the visible light source, and receiving the visible light reflected by the body portion to be tested to acquire the visible image.

For example, in the vascular imaging method provided by an embodiment of the present disclosure, acquiring an infrared image and a visible image comprises: moving a reflecting-mirror to a non-reflective position; emitting the infrared light to the body portion to be tested by an infrared light source, and receiving the infrared light reflected by the body portion to be tested to acquire the infrared image; and emitting the visible light to the body portion to be tested by an visible light source, and receiving the visible light reflected by the body portion to be tested to acquire the visible image.

For example, in the vascular imaging method provided by an embodiment of the present disclosure, projecting the vascular enhancement image to the body portion to be tested comprises: moving a reflecting-mirror to a reflective position; projecting light of the vascular enhancement image by a projection device; and reflecting the light of the vascular enhancement image to the body portion to be tested by the reflecting-mirror.

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly. In order to make the following descriptions of the embodiments of the present disclosure clear and concise, the present disclosure omits detailed descriptions of known functions and known components.

With advancement of society, people's requirements for medical services are constantly increasing; and in order to improve a success rate of venipuncture, medical staff need an auxiliary vein display apparatus, so that a vein may be quickly and accurately positioned by using the vein display apparatus. According to a technology known to the inventor, the vein display apparatus can illuminate a surface of skin by infrared light, and then acquire a vascular image of the surface of the skin; because hemoglobin in the vein and tissue surrounding the vein have difference in absorbing infrared light, thus recognizability of the vein may be enhanced. However, background light in a non-vascular region surrounding the vein still affects clarity of the vein to a certain extent.

At least one embodiment of the present disclosure provides a vascular imaging apparatus, which comprises: a light source device, an image acquisition device, a projection device and an image processor. The light source device is configured to emit visible light and infrared light to a body portion to be tested in a time-sharing manner; the image acquisition device is configured to receive the visible light reflected by the body portion to be tested to acquire a visible image, receive the infrared light reflected by the body portion to be tested to acquire an infrared image, and transmit the infrared image and the visible image to the image processor; the image processor is configured to receive the infrared image and the visible image, and perform image processing on the infrared image and the visible image, to acquire a vascular enhancement image of the body portion to be tested, and the image processor is further configured to transmit the vascular enhancement image to the projection device; the projection device is configured to receive the vascular enhancement image and project the vascular enhancement image onto the body portion to be tested.

At least one embodiment of the present disclosure provides a vascular imaging apparatus and a vascular imaging method, which, by acquiring an infrared image and a visible image of a body portion to be tested and performing image processing on the infrared image and the visible image, eliminates background light of the non-vascular region, so as to enhance contrast between a vascular region and the non-vascular region, and improve recognizability of a blood vessel.

It should be noted that, in descriptions of the present disclosure, a first state and a second state represent states of the vascular imaging apparatus in different working periods. In a case where the vascular imaging apparatus is in the first state, an image acquisition device is configured to acquire the infrared image and the visible image of the body portion to be tested; and in a case where the vascular imaging apparatus is in the second state, a projection device is configured to project a vascular enhancement image to the body portion to be tested.

Several embodiments of the present disclosure are described in details below, but the present disclosure is not limited to these specific embodiments.

Figure 1:
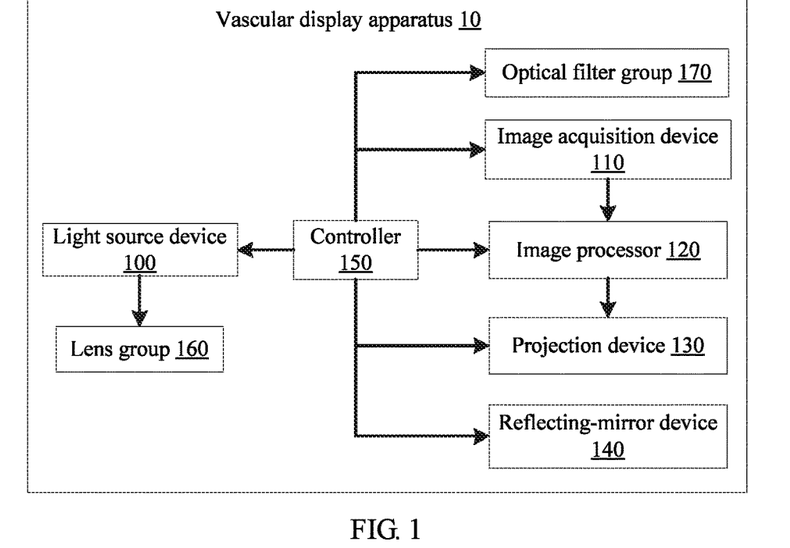
FIG. 1 is a schematic block diagram of a vascular imaging apparatus provided by an embodiment of the present disclosure.
Figure 2A:
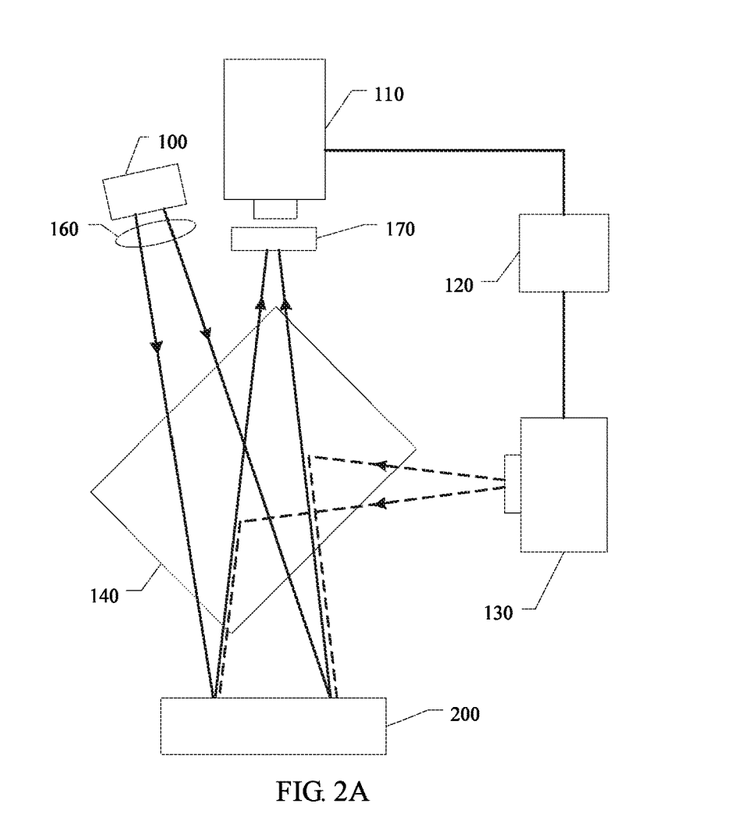
FIG. 2A is a structural schematic diagram of a vascular imaging apparatus in a first state provided by an embodiment of the present disclosure.

FIG. 1 shows a schematic block diagram of a vascular imaging apparatus provided by an embodiment of the present disclosure; FIG. 2A shows a structural schematic diagram of a vascular imaging apparatus in a first state provided by an embodiment of the present disclosure; and FIG. 2B shows a structural schematic diagram of a vascular imaging apparatus in a second state provided by an embodiment of the present disclosure.

Figure 2B:
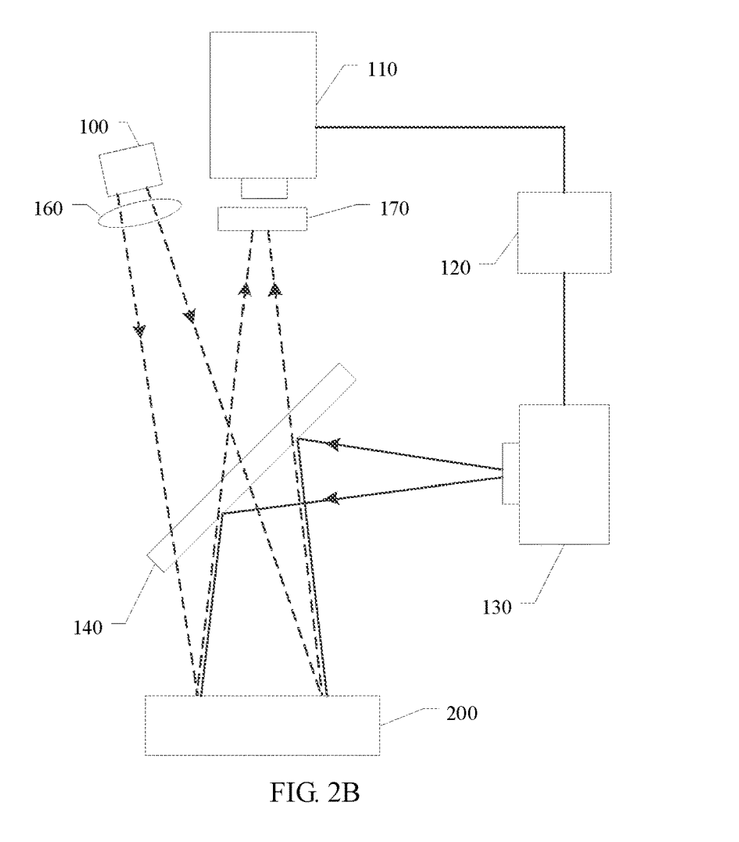
FIG. 2B is a structural schematic diagram of a vascular imaging apparatus in a second state provided by an embodiment of the present disclosure.

For example, as shown in FIG. 1, FIG. 2A and FIG. 2B, the vascular imaging apparatus 10 comprises a light source device 100, an image acquisition device 110, an image processor 120 and a projection device 130. The light source device 100 is configured to emit visible light and infrared light to the body portion to be tested 200 in a time-sharing manner. The image acquisition device 110 is configured to receive the visible light reflected by the body portion to be tested 200 to acquire the visible image, and receive the infrared light reflected by the body portion to be tested 200 to acquire the infrared image, and the image acquisition device 110 is further configured to transmit the infrared image and the visible image to the image processor 120. The image processor 120 is configured to receive the infrared image and the visible image, and perform image processing on the infrared image and the visible image, to acquire a vascular enhancement image of the body portion to be tested 200; and the image processor 120 is further configured to transmit the vascular enhancement image to the projection device 130. The projection device 130 is configured to receive the vascular enhancement image and project the vascular enhancement image onto the body portion to be tested 200.

The vascular imaging apparatus 10 provided by the embodiment of the present disclosure may be used, for example, for displaying a vein in a surface layer of human skin. For example, the vascular imaging apparatus 10 may acquire a vein image in the human skin, and process the vein image to eliminate background light of the non-vascular region, so as to increase contrast between the vascular region and the non-vascular region, and improve recognizability of the vein; the vascular imaging apparatus 10 may further project a display enhanced vein image to a position on the human skin corresponding to the vein in real time, so as to accurately position the vein. Especially for infants, elderly patients, dark-skinned patients, obese patients or other people, whose veins are unclear, the vascular imaging apparatus 10 can improve recognizability of the veins and improve a success rate of venipuncture.

For example, the body portion to be tested 200 may be skin, for example, arm skin, skin of dorsum of hand, skin of dorsum of foot, and the like. Specific positions of the body portion to be tested 200 will not be limited in the embodiments of the present disclosure.

For example, intensity of the infrared light and intensity of the visible light may be the same, and an optical path of the infrared light from the light source device 100 to the body portion to be tested 200 may be the same as an optical path of the visible light from the light source device 100 to the body portion to be tested 200, so as to ensure that infrared light and visible light have the same light intensity distribution on the body portion to be tested 200. Therefore, it may be ensured that a light intensity distribution in the non-vascular region of the infrared image and a light intensity distribution in the non-vascular region of the visible image are substantially the same, and background light of the non-vascular region may be effectively eliminated by processing the infrared image and the visible image, so as to improve recognizability of the blood vessel.

For example, human veins contain hemoglobin, and the hemoglobin is sensitive to infrared light, especially sensitive to near-infrared light, and hemoglobin absorbs and scatters infrared light more than other skin tissues. There is more hemoglobin in the vascular region, less hemoglobin or even no hemoglobin in the non-vascular region, so that infrared light absorbed and scattered by the vascular region is more than infrared light absorbed and scattered by the non-vascular region. Visible light absorbed and scattered by the vascular region has little difference from visible light absorbed and scattered by the non-vascular region. Thus, in the infrared image, a light intensity distribution and light intensity in the vascular region have greater difference from those in the non-vascular region; and in the visible image, a light intensity distribution and light intensity in the vascular region are substantially the same as those in the non-vascular region. Therefore, background light of the non-vascular region may be effectively eliminated by processing the visible image and the infrared image.

For example, the infrared light may be near-infrared light, and the infrared light has a wavelength ranging from 0.85 μm to 0.95 μm. As compared with near-infrared light with other wavelengths, hemoglobin can absorbs more infrared light in the wavelength ranging from 0.85 μm to 0.95 μm, and the infrared light in the wavelength ranging from 0.85 μm to 0.95 μm penetrates deeper in the body portion to be tested 200. The visible light may have a wavelength ranging from 0.63 μm to 0.76 μm, and as compared with visible light with other wavelengths, hemoglobin can absorbs less visible light in the wavelength ranging from 0.63 μm to 0.76 μm. Thus, difference in the light intensity distribution and the light intensity of the vascular region between the infrared image and the visible image may be further increased.

For example, the infrared image and the visible image may both be grayscale images. For example, the vascular enhancement image may also be a grayscale image.

For example, the image processor 120 may be a central processing unit (CPU) or other forms of processing unit having image data processing capabilities and/or program execution capabilities, for example, the image processor 120 may be a graphics processing unit (GPU), a field-programmable gate array (FPGA), a tensor processing unit (TPU), or the like. For another example, the central processing unit (CPU) may be an X86, ARM architecture, or the like.

For example, the image processor 120 may perform image processing on the infrared image and the visible image, to acquire the vascular enhancement image of the body portion to be tested 200. In one example, the image processing may include operations below:

S1: performing vascular recognition processing on the visible image and the infrared image, to respectively acquire a vascular region and a non-vascular region in the infrared image, a vascular region and a non-vascular region in the visible image;

S2: calculating a ratio of an average light intensity value of the non-vascular region in the infrared image to an average light intensity value of the non-vascular region in the visible image;

S3: calculating a product of a light intensity value of the visible image and the ratio, and performing difference processing on a light intensity value of the infrared image and the product, to acquire the vascular enhancement image.

For example, in operation S1, a method of the vascular recognition processing may be a multi-scale Hessian matrix method, an SVM classifier-based deep learning method, and the like. During image processing, a blood vessel may be considered to have a linear or tubular structure. An eigenvalue of a Hessian matrix may be used for detecting an edge of the blood vessel, strength and a direction of the blood vessel, and the like.

For example, performing vascular recognition processing by using the multi-scale Hessian matrix method may include operations below:

Assuming that both the infrared image and the visible image are two-dimensional images, light intensity distributions are respectively I1(x, y) and I2(x, y), where (x, y) are coordinates of respective pixel points in the infrared image or the visible image. I1(x, y) is convoluted with a Gaussian function G(x, y, s) whose variance is $s^2$ to obtain I1'(x, y, s), where I1'(x, y, s) may be expressed as:

$$I1'(x,y,s)=I1(x,y)*G(x,y,s)$$

By seeking second-order partial derivatives of I1'(x, y, s), respective elements of the Hessian matrix may be obtained, and calculation formulas of the respective elements may be:

$$I1_{xx}=I1(x,y)*s^2 G_{xx}$$

$$I1_{yy}=I1(x,y)*s^2 G_{yy}$$

$$I1_{xy}=I1(x,y)*s^2 G_{xy}$$

$$I1_{yx}=I1(x,y)*s^2 G_{yx}$$

Where, Gxx is a second-order partial derivative of the Gaussian function G(x, y, s) with respect to x, Gyy is a second-order partial derivative of the Gaussian function G(x, y, s) with respect to y, Gxy is a second-order partial derivative of the Gaussian function G(x, y, s) by firstly seeking a partial derivative with respect to x and then seeking a partial derivative with respect to y, and Gyx is a second-order partial derivative of the Gaussian function G(x, y, s) by firstly seeking a partial derivative with respect to y and then seeking a partial derivative with respect to x; when both Gxy and Gyx are continuous, results of Gxy and Gyx are the same, so I1xy=I1yx.

Thus, the Hessian matrix of I1(x, y) may be expressed as follows:

$$H(x,y) = \begin{vmatrix} I1_{xx} & I1_{xy} \\ I1_{yx} & I1_{yy} \end{vmatrix} = \begin{vmatrix} I1_{xx} & I1_{xy} \\ I1_{xy} & I1_{yy} \end{vmatrix}$$

Two eigenvalues λ1 and λ2 of the Hessian matrix may be expressed as follows:

$$\lambda_1 = \frac{1}{2}\left[(I1_{xx}+I1_{yy}) - \sqrt{(I1_{xx}-I1_{yy})^2 + 4I1_{xy}^2}\right]$$

$$\lambda_2 = \frac{1}{2}\left[(I1_{xx}+I1_{yy}) + \sqrt{(I1_{xx}-I1_{yy})^2 + 4I1_{xy}^2}\right]$$

Where, $|\lambda_1| \leq |\lambda_2|$. An eigenvector corresponding to a larger one of the two eigenvalues λ1 and λ2 indicates a direction in which a curvature of the pixel point (x, y) is the maximum, and an eigenvector corresponding to a smaller one of the two eigenvalues λ1 and λ2 indicates a direction in which the curvature of the pixel point (x, y) is the minimum.

Based on the eigenvalues of the Hessian matrix, confidence V(s) of the blood vessel may be expressed as follows:

$$V(s) = \begin{cases} 0 & \text{when } \lambda_2 > 0 \\ e^{\left(-\frac{R^2}{2\beta^2}\right)} \cdot \left(1 - e^{\left(-\frac{P^2}{2c^2}\right)}\right) & \text{else} \end{cases}$$

Where, s is a scale factor, $\beta=0.5$, $R=\lambda_1/\lambda_2$, $P=\sqrt{\lambda_1^2+\lambda_2^2}$, c is one-half of a maximum value of P, and $\beta$ and c are proportionality factors respectively affecting R and P.

According to a scale space theory, with respect to a linear structure, when the scale factor s best matches an actual width of the blood vessel, the confidence of the blood vessel reaches the maximum. Multi-scale vascular enhancement is just a method comprising iterating scale factors s for each point in the two-dimensional image, to obtain values of the confidence V(s) of the blood vessel at different scales, and taking the maximum V(s) value as an actual output of the point. Therefore, the confidence of the blood vessel at the pixel point (x, y) is:

$$V = \max_{s_{min} \leq s \leq s_{max}} V(s)$$

Where, $s_{min}$ and $s_{max}$ are respectively a minimum value and a maximum value of s. s may have a value between 1 and 8, and according to a size of a diameter of the blood vessel, s may have different values, for example, s may be 1, 2, 4 or 8. The larger the s is, the larger the c is, then the larger of the diameter of the blood vessel, the greater the response of the blood vessel; the smaller the s is, the smaller the c is, then the smaller of the diameter of the blood vessel, the greater the response of the blood vessel. Finally, V(s) is binarized to distinguish between the vascular region and the non-vascular region in the infrared image. The blood vessel having a larger response indicates that the blood vessel is more easily recognized, that is to say, in a case where the larger the s is, the larger the c is, then the larger of the diameter of the blood vessel, the greater the response of the blood vessel, that is, the blood vessel having the larger diameter is more easily recognized.

For example, after the vascular recognition processing is performed on the infrared image by using the multi-scale Hessian matrix method, the vascular region and the non-vascular region in the infrared image may be obtained. Both the infrared image and the visible image are images of the same body portion to be tested 200, and the vascular region and the non-vascular region in the infrared image respectively correspond to the vascular region and the non-vascular region in the visible image. Thus, the vascular recognition processing may be performed on the visible image based on the vascular region and the non-vascular region of the infrared image, so as to distinguish between the vascular region and the non-vascular region in the visible image.

For example, in operation S2, firstly, an average light intensity value P1 of the non-vascular region of the infrared image I1(x, y) and an average light intensity value P2 of the non-vascular region of the visible image I2(x, y) are calculated; and then a ratio P1/P2 of the average light intensity values of the non-vascular regions in the two images (i.e., the infrared image and the visible image) is calculated.

For example, in operation S3, a product of a light intensity value of the visible image I2(x, y) and the ratio P1/P2 of the average light intensity values of the non-vascular regions is calculated, and then difference processing is performed on a light intensity value of the infrared image I1(x, y) and the product, so as to acquire a vascular image I3(x, y) in which background light of the non-vascular region has been eliminated, and improve contrast between the vascular region and the non-vascular region. For example, I3(x, y) may be expressed as follows:

$$I3(x,y)=I1(x,y)-P1/P2*I2(x,y)$$

Finally, the vascular image I3(x, y) is normalized to acquire a vascular enhancement image I4(x, y). For example, I4(x, y) may be calculated by a formula below:

$$I4(x,y)=a*(I3(x,y)-I3_{min})/(I3(x,y)+I3_{max})$$

Where, $I3_{max}$ and $I3_{min}$ are respectively a maximum value and a minimum value of I3(x, y), and a is a gray level factor. For example, a may be 255, such that a gray level of the vascular enhancement image I4(x, y) ranges from 0 to 255, 255 indicates that the image is white, and 0 indicates that the image is black.

It should be noted that, before the vascular recognition processing is performed, the image processor 120 may further preprocess the infrared image and the visible image, and by preprocessing, irrelevant information or noise information in the infrared image and the visible image may be eliminated, so that the vascular recognition processing is better performed. The operations of preprocessing may include, for example, zooming in and out of the infrared image and the visible image, gamma correction, image enhancement, or noise reduction filtering, and the like.

Figure 3A:
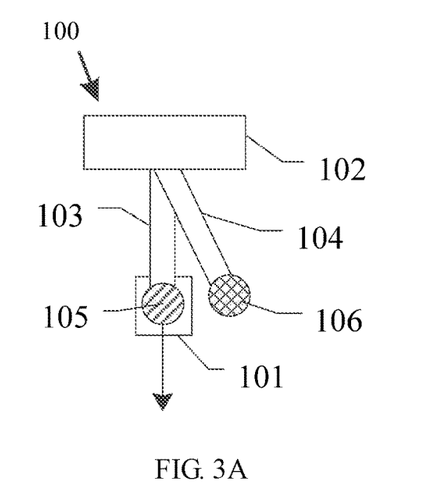
FIG. 3A is a structural schematic diagram of a light source device provided by an embodiment of the present disclosure.
Figure 3B:
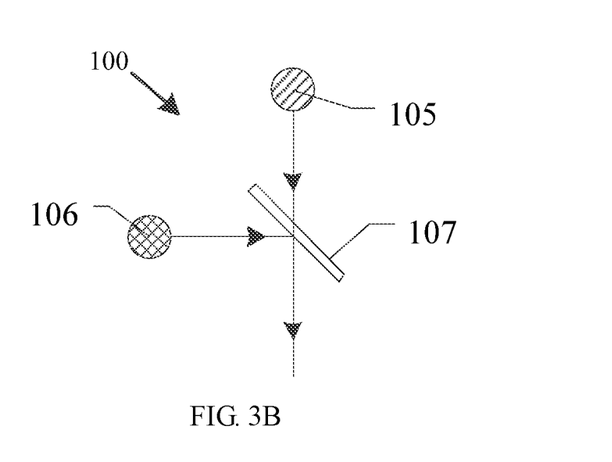
FIG. 3B is a structural schematic diagram of another light source device provided by an embodiment of the present disclosure.

For example, FIG. 3A is a structural schematic diagram of a light source device 100 provided by an embodiment of the present disclosure; FIG. 3B is a structural schematic diagram of another light source device 100 provided by an embodiment of the present disclosure. As shown in FIG. 3A and FIG. 3B, the light source device 100 includes a visible light source 106, an infrared light source 105 and a light source conversion element. The visible light source 106 is configured to emit the visible light. The infrared light source 105 is configured to emit the infrared light. The light source conversion element is configured to allow a position at which the visible light is incident on the body portion to be tested 200 and a position at which the infrared light is incident on the body portion to be tested 200 to be same. For example, the light source conversion element is configured to allow an optical path of the visible light emitted from the light source device 100 and an optical path of the infrared light emitted from the light source device 100 to be the same, that is to say, from the light source device 100 to the body portion to be tested 200, the optical paths of the visible light and the infrared light are the same.

For example, the visible light source 106 and the infrared light source 105 may be light emitting diode (LED) light sources or cathode emission lamps, and the like. For example, the visible light source 106 may be a monochromatic LED light source or a light source consisting of a white light source and an optical filter. The infrared light source 105 may be an infrared LED array, and the like.

For example, the visible light source 106 may include a single visible light source, and may also include a plurality of visible light sources. The infrared light source 105 may include a single infrared light source, and may also include a plurality of infrared light sources.

For example, as shown in FIG. 3A, in an example, the light source conversion element includes a light source driver 102, a first light source connecting rod 103 and a second light source connecting rod 104. One end of the first light source connecting rod 103 is connected with the infrared light source 105, and the other end is connected with the light source driver 102. One end of the second light source connecting rod 104 is connected with the visible light source 106, and the other end is connected with the light source driver 102.

For example, the light source driver 102 is configured to respectively move the infrared light source 105 and the visible light source 106 to a light source target position 101 through the first light source connecting rod 103 and the second light source connecting rod 104. For example, the light source driver 102 may move the visible light source 106 and the infrared light source 105 to the light source target position 101 in a time-sharing manner. Thus, both the infrared light and the visible light are emitted from the light source target position 101, and the optical paths of the visible light and the infrared light are the same.

For example, the light source driver 102 may include a motor, an output shaft, and a transmission component such as a gear, a turbine, and the like. The motor may be a servo motor to implement precise control, so that the visible light source 106 or the infrared light source 105 is accurately moved to the light source target position 101. The first light source connecting rod 103 and the second light source connecting rod 104 may be connected with the output shaft of the light source driver 102 for power transmission.

For example, as shown in FIG. 3B, in another example, the light source conversion element may include a dichroic mirror 107. The infrared light source 105 and the visible light source 106 are symmetrically provided with respect to the dichroic mirror 107, so as to ensure that a light intensity distribution of the visible light incident on the body portion to be tested 200 is the same as a light intensity distribution of the infrared light incident on the body portion to be tested 200. The dichroic mirror 107 is configured to make optical paths of infrared light and visible light emitted through the dichroic mirror 107 be the same. A position at which the infrared light emitted via the dichroic mirror 107 is incident on the body portion to be tested 200 is the same as a position at which the visible light emitted via the dichroic mirror 107 is incident on the body portion to be tested 200. For example, the dichroic mirror 107 is configured to transmit visible light (e.g., visible light having the wavelength ranging from 0.63 μm to 0.76 μm) and to reflect infrared light (e.g., infrared light having the wavelength ranging from 0.85 μm to 0.95 μm), or to reflect visible light (e.g., visible light having the wavelength ranging from 0.63 μm to 0.76 μm) and to transmit infrared light (e.g., infrared light having the wavelength ranging from 0.85 μm to 0.95 μm).

For example, the image acquisition device 110 may be a high sensitivity image sensor, such as a CMOS device or a CCD device.

For example, the projection device 130 may include a liquid crystal display (LCD) projector, a digital light procession (DLP) projector, a liquid crystal on silicon (LCOS) projector, and the like.

For example, light projected by the projection device 130 may be monochromatic light in green or red, etc., so that the vascular enhancement image may be a monochrome grayscale image in green or red, etc., thereby increasing the recognizability of the vascular enhancement image.

For example, as shown in FIGS. 1, 2A and 2B, the vascular imaging apparatus 10 further comprises a reflecting-mirror device 140. The projection device 130 and the image acquisition device 110 are symmetrical with respect to the reflecting-mirror device 140, and the reflecting-mirror device 140 is configured to reflect light projected by the projection device 130 to the body portion to be tested 200. For example, the reflecting-mirror device 140 is disposed at an intersection point of an optical path center line of the light projected by the projection device 130 and an optical path center line of the light incident on the image acquisition device 110. The reflecting-mirror device 140 is configured to reflect the light projected by the projection device 130, such that light, that is reflected, projected by the projection device 130 is incident on the body portion to be tested 200.

For example, as shown in FIG. 2B, in a case where the vascular imaging apparatus 10 is in the second state, the projection device 130 and the image acquisition device 110 are symmetrically provided with respect to a light reflecting surface of the reflecting-mirror device 140, and the projection device 130 and the image acquisition device 110 may have the same field of view and the same magnification, so that a position of an image acquired by the image acquisition device 110 precisely matches a position of an image projected by the projection device 130. Thus, it may be ensured that the vascular enhancement image is accurately projected onto the position of the body portion to be tested 200 corresponding to the vascular enhancement image. That is to say, it is ensured that a position of the blood vessel in the vascular enhancement image coincides with an actual position of the blood vessel on the body portion to be tested 200, so as to improve accuracy of positioning the blood vessels.

Figure 4:
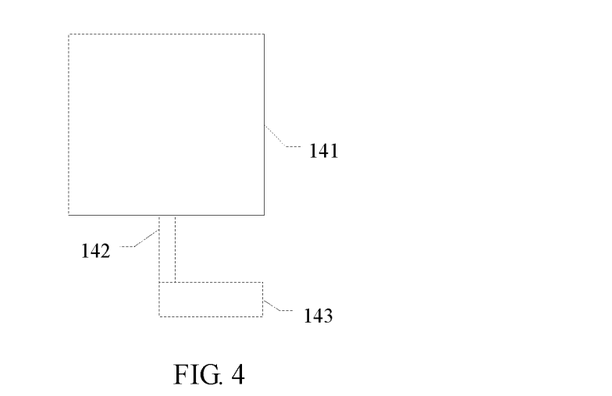
FIG. 4 is a structural schematic diagram of a reflecting-mirror device provided by an embodiment of the present disclosure.

For example, FIG. 4 is a structural schematic diagram of a reflecting-mirror device provided by an embodiment of the present disclosure. As shown in FIG. 4, the reflecting-mirror device 140 may include a reflecting-mirror 141, a reflecting-mirror driver 143 and a reflecting-mirror connecting rod 142. The reflecting-mirror driver 143 is configured to move the reflecting-mirror 141 to a non-reflective position or a reflective position through the reflecting-mirror connecting rod 142. The reflecting-mirror 141 is configured to reflect the light projected by the projection device 130 to the body portion to be tested 200 in a case where the reflecting-mirror 141 is located in the reflective position, and the image acquisition device 110 is configured to receive the visible light or the infrared light reflected by the body portion to be tested 200, in a case where the reflecting-mirror 141 is located in the non-reflective position.

For example, one end of the reflecting-mirror connecting rod 142 is connected with the reflecting-mirror 141, and the other end is connected with the reflecting-mirror driver 143. The reflecting-mirror driver 143 may be a rotary motor, and the like. The reflecting-mirror driver 143 controls the reflecting-mirror 141 to rotate from the non-reflective position to the reflective position, or to rotate from the reflective position to the non-reflective position by the reflecting-mirror connecting rod 142.

For example, the reflecting-mirror 141 may be a planar reflecting-mirror. The reflecting-mirror 141 may have high reflectivity (for example, reflectivity greater than 90%) with respect to the light (for example, red light or green light) projected by the projection device 130. The light reflecting surface of the reflecting-mirror 141 may be coated, for example, with a multilayer dielectric film, to implement high reflection.

For example, as shown in FIGS. 2A and 2B, in a specific example, the reflecting-mirror device 140 includes only one reflecting-mirror 141, but the present disclosure is not limited thereto. An angle and a position of the reflecting-mirror 141, as well as the number of reflecting-mirrors 141 may be set according to actual application needs.

For example, as shown in FIG. 2A, when the vascular imaging apparatus 10 is in a first state, the reflecting-mirror driver 143 controls the reflecting-mirror 141 to rotate, so that the reflecting-mirror driver 143 is located in the non-reflective position. In this case, the light reflecting surface of the reflecting-mirror 141 is parallel to the optical path of the visible light or the optical path of the infrared light, the light source device 100 emits the visible light and the infrared light to the body portion to be tested 200 in a time-sharing manner, and the image acquisition device 110 may receive the visible light or the infrared light reflected by the body portion to be tested 200. As shown in FIG. 2B, in the case where the vascular imaging apparatus 10 is in the second state, the reflecting-mirror driver 143 controls the reflecting-mirror 141 to rotate, so that the reflecting-mirror driver 143 is located in the reflective position. In this case, the light reflecting surface of the reflecting-mirror 141 is provided in the optical path of light projected by the projection device 130, and faces a light exiting side of the projection device 130; the light reflecting surface of the reflecting-mirror 141 is, for example, provided at an angle of 45 degrees to an optical path center line of light projected by the projection device 130, so that the reflecting-mirror 141 may reflect light of the vascular enhancement image projected by the projection device 130 to the body portion to be tested 200.

It should be noted that, both FIG. 2A and FIG. 2B show the optical path of the visible light, the optical path of the infrared light and an optical path of light of the vascular enhancement image. For example, in FIG. 2A, a solid line with an arrow indicates the optical paths of the visible light and the infrared light, a dotted line with an arrow indicates the optical path of the light of the vascular enhancement image projected by the projection device 130; in FIG. 2B, a solid line with an arrow indicates the optical path of the light of the vascular enhancement image projected by the projection device 130, and a dotted line with an arrow indicates the optical paths of the visible light and the infrared light. It should be understood, however, that in the case where the vascular imaging apparatus 10 is in the first state, only the optical path of the visible light or the infrared light exists; and in the case where the vascular imaging apparatus 10 is in the second state, only the optical path of the light of the vascular enhancement image exists. In addition, for clarity, the optical path of the light of the vascular enhancement image and the optical path of the visible light or the infrared light reflected by the body portion to be tested 200 are staggered from each other, but actually, the optical path of the light of the vascular enhancement image is coaxial with the optical paths of the visible light and the infrared light reflected by the body portion to be tested 200, so that the position of the image acquired by the image acquisition device 110 precisely matches the position of the image projected by the projection device 130.

For example, the vascular imaging apparatus 10 may further comprise a lens group 160. The lens group 160 is located on a light exiting side of the light source device 110, and is configured to converge the visible light and the infrared light, so that the visible light and the infrared light are incident on the body portion to be tested 200. For example, when the light source device 110 emits the visible light, the lens group 160 may converge the visible light; and when the light source device 110 emits the infrared light, the lens group 160 may converge the infrared light.

For example, in the light source device 110 shown in FIG. 3A, the light source target position 101 may be located at a focus of the lens group 160; in the light source device 110 shown in FIG. 3B, the infrared light source 105 may be provided at the focus of the lens group 160; because the infrared light source 105 and the visible light source 106 are symmetrically provided with respect to the dichroic mirror 107, the visible light source 106 is also substantially located at the focus of the lens group 160. Thus, the lens group 160 may converge the visible light and the infrared light emitted from the light source device 110, to obtain converged visible light and converged infrared light, and then the converged visible light and the converged infrared light are incident on the body portion to be tested 200. For example, the converged visible light and the converged infrared light may be incident onto the body portion to be tested 200 perpendicularly. For another example, the converged visible light and the converged infrared light may also be incident onto the body portion to be tested 200 at a certain angle; and an incident angle of the converged visible light and an incident angle of the converged infrared light may be designed according to actual application needs, as long as the converged visible light and the converged infrared light may be incident on the body portion to be tested 200, which will not be specifically limited in the embodiment of the present disclosure.

For example, as shown in FIG. 2A and FIG. 2B, in a specific example, the lens group 160 includes a convex lens, but the present disclosure is not limited thereto. The lens group 160 may also include a concave lens, a convex lens, a combination thereof, and the like, and the number, positional relationship, and the like of concave lenses and convex lenses, may be designed according to actual application needs, provided that the visible light and the infrared light may be incident on the body portion to be tested 200.

For example, the vascular imaging apparatus 10 further comprises an optical filter group 170. As shown in FIG. 2A and FIG. 2B, the optical filter group 170 is provided at an image input end of the image acquisition device 110. The optical filter group 170 is configured to be capable of transmit light with a specific wavelength. For example, the optical filter group 170 includes an infrared light filter, a visible light filter, and an optical filter driver. The infrared light filter is configured to transmit the infrared light, for example, to transmit infrared light with a wavelength ranging from 0.85 μm to 0.95 μm; the visible light filter is configured to transmit the visible light, for example, to transmit the visible light with a wavelength ranging from 0.63 μm to 0.76 μm. Therefore, the optical filter group 170 may filter out stray light in an environment and reduce noise signals of the visible image and the infrared image.

For example, the optical filter driver is configured to move the visible light filter to the image input end of the image acquisition device 110 in a case where the light source device 110 emits the visible light; and the optical filter driver is further configured to move the infrared light filter to the image input end of the image acquisition device 110, in a case where the light source device 110 emits the infrared light.

For example, as shown in FIG. 1, the vascular imaging apparatus 10 further comprises a controller 150. The controller 150 is configured to control related components (e.g., the light source device 100, the reflecting-mirror device 140 and the optical filter group 170) in the vascular imaging apparatus 10 to perform desired functions. For example, the controller 150 is configured to control the light source device 100 to emit the visible light and the infrared light in a time-sharing manner. The controller 150 is further configured to make respective components work together, so as to respectively acquire the infrared image and the visible image. For example, when the vascular imaging apparatus 10 is in the first state, the controller 150 may control the reflecting-mirror device 140, so that the reflecting-mirror 141 is located in the non-reflective position; the controller 150 may further control the light source device 100 to emit the infrared light; meanwhile, the controller 150 may further control the optical filter group 170, so that the infrared light filter is moved to the image input end of the image acquisition device 110. Thus, the image acquisition device 110 may receive the infrared light reflected from the body portion to be tested 200, to acquire the infrared image.

For example, a signal connection may be implemented between the controller 150 and related components of the vascular imaging apparatus 10 in a wired or wireless manner.

For example, the controller 150 may be implemented by software, hardware, firmware, or any combination thereof, and specific implementations (e.g., software programming, FPGA programming, etc.) will not be described in detail herein. For example, the controller 150 may be implemented by hardware, for example, formed in a chip; the controller 150 may further be implemented by a processor and a memory; the memory stores executable computer program that implements a control function and data required during executing the computer program or data generated by executing the computer program. For another example, the function of the controller 150 may be implemented by a fixed electronic apparatus (e.g., a desktop computer), or, the function of the controller 150 may further be implemented by a mobile electronic apparatus (e.g., a mobile phone, a tablet personal computer, etc.), which will not be specifically limited in the embodiment of the present disclosure.

Figure 5:
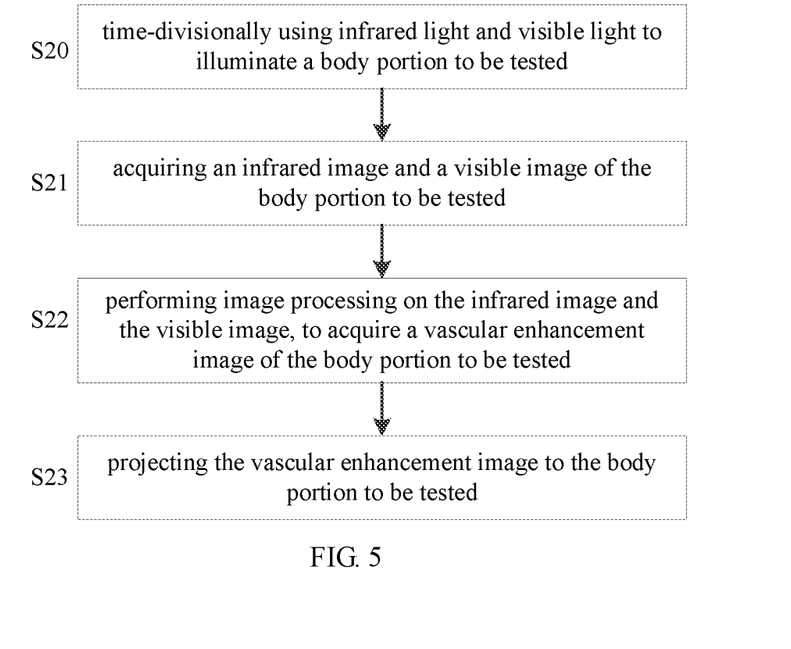
FIG. 5 is a schematic flow chart of a vascular imaging method provided by an embodiment of the present disclosure.

FIG. 5 is a schematic flow chart of a vascular imaging method provided by an embodiment of the present disclosure.

For example, as shown in FIG. 5, the vascular imaging method provided by the embodiment of the present disclosure comprises steps of:

S20: time-divisionally using infrared light and visible light to illuminate a body portion to be tested;

S21: acquiring an infrared image and a visible image of the body portion to be tested;

S22: performing image processing on the infrared image and the visible image, to acquire a vascular enhancement image of the body portion to be tested; and S23: projecting the vascular enhancement image to the body portion to be tested.

The vascular imaging method provided by the embodiment of the present disclosure, by acquiring the infrared image and the visible image at the body portion to be tested and performing image processing on the infrared image and the visible image, effectively eliminates background light of a non-vascular region, enhances contrast between a vascular region and the non-vascular region, and improves recognizability of a blood vessel.

For example, the vascular imaging method may be used for displaying a vein, so as to display an image of the vein on the body portion to be tested clearly and in real time, and improve a success rate of venipuncture.

For example, for description of the body portion to be tested, infrared light and visible light, reference may be made to the related descriptions of the embodiment of the vascular imaging apparatus, and similar descriptions will be omitted here.

For example, in the operation S21, in one example, in a case where a light source device includes a visible light source, an infrared light source, a light source driver, a first light source connecting rod and a second light source connecting rod, that is, in a case where the light source device has a structure shown in FIG. 3A, acquiring an infrared image and a visible image of the body portion to be tested includes operations below:

S210: moving a reflecting-mirror to a non-reflective position;

S211: moving the infrared light source to a light source target position, emitting the infrared light to the body portion to be tested by the infrared light source, and receiving the infrared light reflected by the body portion to be tested to acquire the infrared image;

S212: moving the visible light source to the light source target position, emitting the visible light to the body portion to be tested by the visible light source, and receiving the visible light reflected by the body portion to be tested to acquire the visible image.

For example, in the operation S21, in another example, in a case where the light source device includes the visible light source, the infrared light source and a dichroic mirror, that is, in a case where the light source device has the structure shown in FIG. 3B, acquiring an infrared image and a visible image of the body portion to be tested includes operations below:

S213: moving the reflecting-mirror to the non-reflective position;

S214: emitting the infrared light to the body portion to be tested by the infrared light source, and receiving the infrared light reflected by the body portion to be tested to acquire the infrared image;

S215: emitting the visible light to the body portion to be tested by the visible light source, and receiving the visible light reflected by the body portion to be tested to acquire the visible image.

For example, before performing the operation S211 or the operation S214, the vascular imaging method further comprises an operation below: moving the infrared light filter to an image input end of an image acquisition device; and before performing the operation S212 or the operation S215, the vascular imaging method further comprises an operation below: moving the visible light filter to the image input end of the image acquisition device.

For example, the controller may control respective related components to work collaboratively, to acquire the infrared image and the visible image respectively. For example, the controller may control to move the reflecting-mirror to the non-reflective position. For another example, the controller may control to move the infrared light source and the visible light source to the light source target position; or, the controller may control the infrared light source and the visible light source to emit light in a time-sharing manner.

For example, the infrared light and the visible light may be received by the image acquisition device to respectively acquire the infrared image and the visible image. The image acquisition device may be, for example, a CMOS image sensor or a CCD image sensor.

For example, in the operation S22, in one example, performing image processing on the infrared image and the visible image may include operations below:

S220: performing vascular recognition processing on the visible image and the infrared image;

S221: calculating a ratio of an average light intensity value of a non-vascular region in the infrared image to an average light intensity value of a non-vascular region in the visible image;

S222: calculating a product of a light intensity value of the visible image and the ratio, and performing difference processing on a light intensity value of the infrared image and the product.

For example, a method of the vascular recognition processing may be a multi-scale Hessian matrix method, so as to improve accuracy of vascular recognition. A method of the vascular recognition processing may further be an SVM classifier-based deep learning method, and the like.

It should be noted that, for specific procedures concerning operation S220, operation S221 and operation S222, reference may be made to the related descriptions of the operation S1, the operation S2 and the operation S3 in the embodiment of the vascular imaging apparatus respectively, and repeated portions will not be described herein again.

For example, in the operation S23, in one example, the projecting the vascular enhancement image to the body portion to be tested includes operations below:

S230: moving a reflecting-mirror to a reflective position;

S231: projecting light of the vascular enhancement image by a projection device; and S232: reflecting the light of the vascular enhancement image to the body portion to be tested by the reflecting-mirror.

For example, the controller may control to move the reflecting-mirror to the reflective position.

For example, for description of the projection device, reference may be made to the related description in the embodiment of the vascular imaging apparatus, and repeated portions will be omitted herein.

For the present disclosure, the following statements should be noted:

(1) the accompanying drawings of the embodiment(s) of the present disclosure involve only the structure(s) in connection with the embodiment(s) of the present disclosure, and other structure(s) can be referred to common design(s); and (2) In case of no conflict, the embodiments of the present disclosure and the features in the embodiment(s) can be combined with each other to obtain new embodiment(s).

What have been described above are only specific implementations of the present disclosure, the protection scope of the present disclosure is not limited thereto, and the protection scope of the present disclosure should be based on the protection scope of the claims.

What is claimed is:

1. A vascular imaging apparatus, comprising:
   a light source device,
   an image acquisition device,
   a projection device, and
   an image processor,
   wherein the light source device is configured to emit visible light and infrared light to a body portion to be tested in a time-sharing manner;
   wherein the image acquisition device is configured to receive the visible light reflected by the body portion to be tested to acquire a visible image, receive the infrared light reflected by the body portion to be tested to acquire an infrared image, and transmit the infrared image and the visible image to the image processor;
   wherein the image processor is configured to receive the infrared image and the visible image, and perform image processing on the infrared image and the visible image, to acquire a vascular enhancement image of the body portion to be tested, and the image processor is further configured to transmit the vascular enhancement image to the projection device;
   wherein the projection device is configured to receive the vascular enhancement image and project the vascular enhancement image onto the body portion to be tested;
   wherein the image processing performed by the image processor to acquire the vascular enhancement image comprises:
      performing vascular recognition processing on the visible image and the infrared image, to respectively acquire a first vascular region and a first non-vascular region in the infrared image, a second vascular region and a second non-vascular region in the visible image,
      calculating a ratio of an average light intensity value of the first non-vascular region in the infrared image to an average light intensity value of the second non-vascular region in the visible image, and
      calculating a product of a light intensity value of the visible image and the ratio, and perform different processing on a light intensity value of the infrared image and the product, to acquire the vascular enhancement image.

2. The vascular imaging apparatus according to claim 1, wherein the vascular recognition processing comprises a multi-scale Hessian matrix method.

3. The vascular imaging apparatus according to claim 1, wherein the light source device comprises a visible light source, an infrared light source and a light source conversion element,
   the visible light source is configured to emit the visible light, the infrared light source is configured to emit the infrared light, and the light source conversion element is configured to allow a position at which the visible light is incident on the body portion to be tested and a position at which the infrared light is incident on the body portion to be tested to be same.

4. The vascular imaging apparatus according to claim 3, wherein the light source conversion element comprises a light source driver, a first light source connecting rod and a second light source connecting rod,
   a first end of the first light source connecting rod is connected with the infrared light source, and a second end of the first light source connecting rod is connected with the light source driver,
   a first end of the second light source connecting rod is connected with the visible light source, and a second end of the second light source connecting rod is connected with the light source driver, and
   the light source driver is configured to move the visible light source or the infrared light source to a light source target position in a time-sharing manner.

5. The vascular imaging apparatus according to claim 3, wherein the light source conversion element comprises a dichroic mirror,
   the infrared light source and the visible light source are symmetrically provided with respect to the dichroic mirror,
   a position at which the infrared light emitted via the dichroic mirror is incident on the body portion to be tested is identical to a position at which the visible light emitted via the dichroic mirror is incident on the body portion to be tested.

6. The vascular imaging apparatus according to claim 1, further comprising a reflecting-mirror device,
   wherein the projection device and the image acquisition device are symmetrical with respect to the reflecting-mirror device, and the reflecting-mirror device is configured to reflect light projected by the projection device to the body portion to be tested.

7. The vascular imaging apparatus according to claim 6, wherein the reflecting-mirror device comprises a reflecting-mirror, a reflecting-mirror driver and a reflecting-mirror connecting rod,
- a first end of the reflecting-mirror connecting rod is connected with the reflecting-mirror, and a second end of the reflecting-mirror connecting rod is connected with the reflecting-mirror driver,
- the reflecting-mirror driver is configured to move the reflecting-mirror to a non-reflective position or a reflective position,
- the reflecting-mirror is configured to reflect the light projected by the projection device to the body portion to be tested in a case where the reflecting-mirror is located in the reflective position, and
- the image acquisition device is configured to receive the visible light or the infrared light reflected by the body portion to be tested in a case where the reflecting-mirror is located in the non-reflective position.

8. The vascular imaging apparatus according to claim 6, wherein the light projected by the projection device is red light or green light.

9. The vascular imaging apparatus according to claim 1, further comprising a lens group,
- wherein the lens group is located on a light exiting side of the light source device, and is configured to converge the visible light and the infrared light.

10. The vascular imaging apparatus according to claim 1, further comprising an optical filter group,
- wherein the optical filter group comprises an infrared light filter, a visible light filter and an optical filter driver,
- the optical filter driver is configured to move the visible light filter to an image input end of the image acquisition device in a case where the light source device emits the visible light, and
- the optical filter driver is configured to move the infrared light filter to the image input end of the image acquisition device in a case where the light source device emits the infrared light.

11. The vascular imaging apparatus according to claim 1, wherein the visible light has a wavelength ranging from 0.63 μm to 0.76 μm, and the infrared light has a wavelength ranging from 0.85 μm to 0.95 μm.

12. The vascular imaging apparatus according to claim 1, further comprising a controller,
- wherein the controller is configured to control the light source device to emit the visible light and the infrared light in a time-sharing manner.

13. A vascular imaging method, comprising:
- time-divisionally using infrared light and visible light to illuminate a body portion to be tested;
- acquiring an infrared image and a visible image of the body portion to be tested;
- performing image processing on the infrared image and the visible image, to acquire a vascular enhancement image of the body portion to be tested; and
- projecting the vascular enhancement image to the body portion to be tested;
- wherein performing image processing to acquire a vascular enhancement image comprises:
  - performing vascular recognition processing on the visible image and the infrared image;
  - calculating a ratio of an average light intensity value of a first non-vascular region in the infrared image to an average light intensity value of a second non-vascular region in the visible image; and
  - calculating a product of a light intensity value of the visible image and the ratio, and performing difference processing on a light intensity value of the infrared image and the product.

14. The vascular imaging method according to claim 13, wherein the vascular recognition processing comprises a multi-scale Hessian matrix method.

15. The vascular imaging method according to claim 13, wherein acquiring an infrared image and a visible image comprises:
- moving a reflecting-mirror to a non-reflective position;
- moving an infrared light source to a light source target position, emitting the infrared light to the body portion to be tested by the infrared light source, and receiving the infrared light reflected by the body portion to be tested to acquire the infrared image; and
- moving a visible light source to the light source target position, emitting the visible light to the body portion to be tested by the visible light source, and receiving the visible light reflected by the body portion to be tested to acquire the visible image.

16. The vascular imaging method according to claim 13, wherein acquiring an infrared image and a visible image comprises:
- moving a reflecting-mirror to a non-reflective position;
- emitting the infrared light to the body portion to be tested by an infrared light source, and receiving the infrared light reflected by the body portion to be tested to acquire the infrared image; and
- emitting the visible light to the body portion to be tested by a visible light source, and receiving the visible light reflected by the body portion to be tested to acquire the visible image.

17. The vascular imaging method according to claim 13, wherein projecting the vascular enhancement image to the body portion to be tested comprises:
- moving a reflecting-mirror to a reflective position;
- projecting light of the vascular enhancement image by a projection device; and
- reflecting the light of the vascular enhancement image to the body portion to be tested by the reflecting-mirror.

* * * * *